US009799201B2

(12) United States Patent
Hazzard et al.

(10) Patent No.: US 9,799,201 B2
(45) Date of Patent: Oct. 24, 2017

(54) WATER HEATER LEAK DETECTION SYSTEM

(71) Applicant: Honeywell International Inc., Morris Plains, NJ (US)

(72) Inventors: Frederick Hazzard, Plymouth, MN (US); Ravindra Khosla, Maple Grove, MN (US); David Heil, Robbinsdale, MN (US)

(73) Assignee: Honeywell International Inc., Morris Plains, NJ (US)

(*) Notice: Subject to any disclaimer, the term of this patent is extended or adjusted under 35 U.S.C. 154(b) by 0 days.

(21) Appl. No.: 15/061,520

(22) Filed: Mar. 4, 2016

(65) Prior Publication Data

US 2016/0260312 A1 Sep. 8, 2016

Related U.S. Application Data

(60) Provisional application No. 62/128,956, filed on Mar. 5, 2015.

(51) Int. Cl.
*G08B 21/00* (2006.01)
*G08B 21/20* (2006.01)
(Continued)

(52) U.S. Cl.
CPC ............... *G08B 21/20* (2013.01); *G01M 3/16* (2013.01); *G08B 3/10* (2013.01); *G08B 25/08* (2013.01); *G01N 27/223* (2013.01)

(58) Field of Classification Search
CPC .......... G08B 21/20; G08B 3/10; G08B 25/08; G01M 3/16; G01N 27/223
(Continued)

(56) References Cited

U.S. PATENT DOCUMENTS

| 2,331,718 A | 10/1943 | Newton |
| 2,920,126 A | 1/1960 | Hajny |

(Continued)

FOREIGN PATENT DOCUMENTS

| CA | 2158120 | 3/1997 |
| CN | 201772614 | 3/2011 |

(Continued)

OTHER PUBLICATIONS

"Results and Methodology of the Engineering Analysis for Residential Water Heater Efficiency Standards," 101 pages, Oct. 1998.

(Continued)

*Primary Examiner* — Ojiako Nwugo
(74) *Attorney, Agent, or Firm* — Seager, Tufte & Wickhem, LLP

(57) ABSTRACT

The disclosure reveals a system for detecting moisture or water in a particular location. The system may incorporate a moisture detector having a control module connected to an appliance, a moisture detection circuit connected to the control module, and a voltage source connected to the moisture detection circuit and to the control module. The voltage source and the moisture detection circuit may provide voltage levels to the control module when the moisture detection circuit detects dry or wet conditions, or conditions between those conditions. A voltage level to the control module may indicate whether the appliance, such as a water heater, a washing machine, or a dish washer, has a leak. If the leak is deemed by a voltage level from the circuit to be worthy of concern, then a display, an alarm, a message, or other notice mechanism may indicate an issue or what action needs to be taken.

15 Claims, 13 Drawing Sheets

(51) Int. Cl.
  *G01M 3/16* (2006.01)
  *G08B 3/10* (2006.01)
  *G08B 25/08* (2006.01)
  *G01N 27/22* (2006.01)

(58) Field of Classification Search
  USPC .................................................. 340/604, 522
  See application file for complete search history.

(56) References Cited

U.S. PATENT DOCUMENTS

| | | |
|---|---|---|
| 3,272,432 A | 9/1966 | Davidson |
| 3,759,279 A | 9/1973 | Smith, Jr. |
| 3,833,428 A | 9/1974 | Snyder et al. |
| 3,847,350 A | 11/1974 | Thompson |
| 3,849,350 A | 11/1974 | Matsko |
| 3,909,816 A | 9/1975 | Teeters |
| 3,948,439 A | 4/1976 | Heeger |
| 4,127,380 A | 11/1978 | Straitz, III |
| 4,131,413 A | 12/1978 | Ryno |
| 4,221,557 A | 9/1980 | Jalics |
| 4,305,547 A | 12/1981 | Cohen |
| 4,324,207 A | 4/1982 | Leuthard |
| 4,324,944 A | 4/1982 | Weihrich et al. |
| RE30,936 E | 5/1982 | Kmetz et al. |
| 4,333,002 A | 6/1982 | Kozak |
| 4,421,062 A | 12/1983 | Padilla, Sr. |
| 4,438,728 A | 3/1984 | Fracaro |
| 4,467,178 A | 8/1984 | Swindle |
| 4,483,672 A | 11/1984 | Wallace et al. |
| 4,507,938 A | 4/1985 | Hama et al. |
| 4,508,261 A | 4/1985 | Blank |
| 4,511,790 A | 4/1985 | Kozak |
| 4,568,821 A | 2/1986 | Boe |
| 4,588,875 A | 5/1986 | Kozak et al. |
| 4,638,789 A | 1/1987 | Ueki et al. |
| 4,655,705 A | 4/1987 | Shute et al. |
| 4,692,598 A | 9/1987 | Yoshida et al. |
| 4,696,639 A | 9/1987 | Bohan, Jr. |
| 4,734,658 A | 3/1988 | Bohan, Jr. |
| 4,742,210 A | 5/1988 | Tsuchiyama et al. |
| 4,770,629 A | 9/1988 | Bohan, Jr. |
| 4,778,378 A | 10/1988 | Dolnick et al. |
| 4,830,601 A | 5/1989 | Dahlander et al. |
| 4,834,284 A | 5/1989 | Vandermeyden |
| 4,906,337 A | 3/1990 | Palmer |
| 4,965,232 A | 10/1990 | Mauleon et al. |
| 4,977,885 A | 12/1990 | Herweyer et al. |
| 4,984,981 A | 1/1991 | Pottebaum |
| 4,986,468 A | 1/1991 | Deisinger |
| 5,007,156 A | 4/1991 | Hurtgen |
| 5,037,291 A | 8/1991 | Clark |
| 5,077,550 A | 12/1991 | Cormier |
| 5,103,078 A | 4/1992 | Boykin et al. |
| 5,112,217 A | 5/1992 | Ripka et al. |
| 5,125,068 A | 6/1992 | McNair et al. |
| 5,126,721 A | 6/1992 | Butcher et al. |
| 5,222,888 A | 6/1993 | Jones et al. |
| 5,232,582 A | 8/1993 | Takahashi et al. |
| 5,236,328 A | 8/1993 | Tate et al. |
| 5,280,802 A | 1/1994 | Comuzie, Jr. |
| 5,317,670 A | 5/1994 | Elia |
| 5,391,074 A | 2/1995 | Meeker |
| 5,424,554 A | 6/1995 | Marran et al. |
| 5,442,157 A | 8/1995 | Jackson |
| 5,567,143 A | 10/1996 | Servidio |
| 5,622,200 A | 4/1997 | Schulze |
| 5,660,328 A | 8/1997 | Momber |
| 5,779,143 A | 7/1998 | Michaud et al. |
| 5,791,890 A | 8/1998 | Maughan |
| 5,797,358 A | 8/1998 | Brandt et al. |
| 5,857,845 A | 1/1999 | Paciorek |
| 5,896,089 A | 4/1999 | Bowles |
| 5,968,393 A | 10/1999 | Demaline |
| 5,971,745 A | 10/1999 | Bassett et al. |
| 5,975,884 A | 11/1999 | Dugger |
| 6,053,130 A | 4/2000 | Shellenberger |
| 6,059,195 A | 5/2000 | Adams et al. |
| 6,069,998 A | 5/2000 | Barnes et al. |
| 6,075,923 A | 6/2000 | Wu |
| 6,080,971 A | 6/2000 | Seitz et al. |
| 6,208,806 B1 | 3/2001 | Langford |
| 6,212,894 B1 | 4/2001 | Brown et al. |
| 6,236,321 B1 | 5/2001 | Troost, IV |
| 6,261,087 B1 | 7/2001 | Bird et al. |
| 6,271,505 B1 | 8/2001 | Henderson |
| 6,286,464 B1 | 9/2001 | Abraham et al. |
| 6,293,471 B1 | 9/2001 | Stettin et al. |
| 6,299,433 B1 | 10/2001 | Gauba et al. |
| 6,350,967 B1 | 2/2002 | Scott |
| 6,351,603 B2 | 2/2002 | Waithe et al. |
| 6,363,218 B1 | 3/2002 | Lowenstein et al. |
| 6,371,057 B1 | 4/2002 | Henderson |
| 6,375,087 B1 | 4/2002 | Day et al. |
| 6,390,029 B2 | 5/2002 | Alphs |
| RE37,745 E | 6/2002 | Brandt et al. |
| 6,410,842 B1 | 6/2002 | McAlonan |
| 6,455,820 B2 | 9/2002 | Bradenbaugh |
| 6,553,946 B1 | 4/2003 | Abraham et al. |
| 6,560,409 B2 | 5/2003 | Troost, IV |
| 6,606,968 B2 | 8/2003 | Iwamam et al. |
| 6,629,021 B2 | 9/2003 | Cline et al. |
| 6,631,622 B1 | 10/2003 | Ghent et al. |
| 6,633,726 B2 | 10/2003 | Bradenbaugh |
| 6,684,821 B2 | 2/2004 | Lannes et al. |
| 6,701,874 B1 | 3/2004 | Schultz et al. |
| 6,732,677 B2 | 5/2004 | Donnelly et al. |
| 6,794,771 B2 | 9/2004 | Orloff |
| 6,795,644 B2 | 9/2004 | Bradenbaugh |
| 6,835,307 B2 | 12/2004 | Talbert et al. |
| 6,845,110 B2 | 1/2005 | Gibson |
| 6,861,621 B2 | 3/2005 | Ghent |
| 6,880,493 B2 | 4/2005 | Clifford |
| 6,920,377 B2 | 7/2005 | Chian |
| 6,934,862 B2 | 8/2005 | Sharood et al. |
| 6,936,798 B2 | 8/2005 | Moreno |
| 6,955,301 B2 | 10/2005 | Munsterhuis et al. |
| 6,959,876 B2 | 11/2005 | Chian et al. |
| 6,967,565 B2 | 11/2005 | Lingemann |
| 6,973,819 B2 | 12/2005 | Ruhland et al. |
| 6,995,301 B1 | 2/2006 | Shorrosh |
| 7,032,542 B2 | 4/2006 | Donnelly et al. |
| 7,065,431 B2 | 6/2006 | Patterson et al. |
| 7,076,373 B1 | 7/2006 | Munsterhuis et al. |
| 7,088,238 B2 | 8/2006 | Karaoguz et al. |
| 7,103,272 B2 | 9/2006 | Baxter |
| 7,117,825 B2 | 10/2006 | Phillips |
| 7,137,373 B2 | 11/2006 | Seymour, II et al. |
| 7,162,150 B1 | 1/2007 | Welch et al. |
| 7,167,813 B2 | 1/2007 | Chian et al. |
| 7,221,862 B1 | 5/2007 | Miller et al. |
| 7,252,502 B2 | 8/2007 | Munsterhuis |
| 7,255,285 B2 | 8/2007 | Troost et al. |
| 7,298,968 B1 | 11/2007 | Boros et al. |
| 7,317,265 B2 | 1/2008 | Chian et al. |
| 7,346,274 B2 | 3/2008 | Bradenbaugh |
| 7,373,080 B2 | 5/2008 | Baxter |
| 7,380,522 B2 | 6/2008 | Krell et al. |
| 7,432,477 B2 | 10/2008 | Teti |
| 7,434,544 B2 | 10/2008 | Donnelly et al. |
| 7,469,550 B2 | 12/2008 | Chapman, Jr. et al. |
| 7,506,617 B2 | 3/2009 | Paine |
| 7,526,539 B1 | 4/2009 | Hsu |
| 7,603,204 B2 | 10/2009 | Patterson et al. |
| 7,613,855 B2 | 11/2009 | Phillips et al. |
| 7,623,771 B2 | 11/2009 | Lentz et al. |
| 7,634,976 B2 | 12/2009 | Gordon et al. |
| 7,672,751 B2 | 3/2010 | Patterson et al. |
| 7,712,677 B1 | 5/2010 | Munsterhuis et al. |
| 7,744,007 B2 | 6/2010 | Beagen et al. |
| 7,744,008 B2 | 6/2010 | Chapman, Jr. et al. |
| 7,770,807 B2 | 8/2010 | Robinson et al. |
| 7,798,107 B2 | 9/2010 | Chian et al. |
| 7,804,047 B2 | 9/2010 | Zak et al. |

(56) References Cited

U.S. PATENT DOCUMENTS

| | | |
|---|---|---|
| 7,902,959 B2 | 3/2011 | Yamada et al. |
| 7,932,480 B2 | 4/2011 | Gu et al. |
| 7,934,662 B1 | 5/2011 | Jenkins |
| 7,970,494 B2 | 6/2011 | Fima |
| 7,974,527 B1 | 7/2011 | Adler |
| 8,061,308 B2 | 11/2011 | Phillips |
| 8,074,894 B2 | 12/2011 | Beagen |
| 8,083,104 B2 | 12/2011 | Roetker et al. |
| 8,111,980 B2 | 2/2012 | Bradenbaugh |
| 8,165,726 B2 | 4/2012 | Nordberg et al. |
| 8,204,633 B2 | 6/2012 | Harbin, III et al. |
| 8,245,987 B2 | 8/2012 | Hazzard et al. |
| 8,322,312 B2 | 12/2012 | Strand |
| 8,360,334 B2 | 1/2013 | Nold et al. |
| 8,367,984 B2 | 2/2013 | Besore |
| 8,422,870 B2 | 4/2013 | Nelson et al. |
| 8,485,138 B2 | 7/2013 | Leeland et al. |
| 8,498,527 B2 | 7/2013 | Roetker et al. |
| 8,600,556 B2 | 12/2013 | Nesler et al. |
| 8,606,092 B2 | 12/2013 | Amiran et al. |
| 8,660,701 B2 | 2/2014 | Phillips et al. |
| 8,667,112 B2 | 3/2014 | Roth et al. |
| 8,726,789 B2 | 5/2014 | Clark |
| 8,770,152 B2 | 7/2014 | Leeland et al. |
| 9,080,769 B2 | 7/2015 | Bronson et al. |
| 9,122,283 B2 | 9/2015 | Rylski et al. |
| 9,195,242 B2 | 11/2015 | Zobrist et al. |
| 9,228,746 B2 | 1/2016 | Hughes et al. |
| 9,249,986 B2 | 2/2016 | Hazzard et al. |
| 9,268,342 B2 | 2/2016 | Beyerle et al. |
| 9,310,098 B2 | 4/2016 | Buescher et al. |
| 2002/0099474 A1 | 7/2002 | Khesin |
| 2003/0093186 A1 | 5/2003 | Patterson et al. |
| 2004/0042772 A1 | 3/2004 | Whitford et al. |
| 2004/0079749 A1 | 4/2004 | Young et al. |
| 2006/0007008 A1* | 1/2006 | Kates ............... G01M 3/002 340/605 |
| 2006/0027571 A1 | 2/2006 | Miyoshi et al. |
| 2006/0272830 A1 | 12/2006 | Fima |
| 2007/0023333 A1 | 2/2007 | Mouhebaty et al. |
| 2007/0210177 A1 | 9/2007 | Karasek |
| 2007/0292810 A1 | 12/2007 | Maiello et al. |
| 2008/0003530 A1 | 1/2008 | Donnelly et al. |
| 2008/0023564 A1 | 1/2008 | Hall |
| 2008/0048046 A1 | 2/2008 | Wagner et al. |
| 2008/0188995 A1 | 8/2008 | Hotton et al. |
| 2008/0197206 A1 | 8/2008 | Murakami et al. |
| 2009/0117503 A1 | 5/2009 | Cain |
| 2010/0065764 A1 | 3/2010 | Canpolat |
| 2010/0163016 A1 | 7/2010 | Pan |
| 2011/0254661 A1* | 10/2011 | Fawcett ............ G08B 13/1445 340/5.61 |
| 2011/0259322 A1 | 10/2011 | Davis et al. |
| 2011/0305444 A1 | 12/2011 | Pussell |
| 2012/0060771 A1 | 3/2012 | Brian et al. |
| 2012/0060829 A1 | 3/2012 | DuPlessis et al. |
| 2013/0104814 A1 | 5/2013 | Reyman |
| 2014/0060457 A1 | 3/2014 | Hill et al. |
| 2014/0202549 A1 | 7/2014 | Hazzard et al. |
| 2014/0203093 A1 | 7/2014 | Young et al. |
| 2014/0212821 A1 | 7/2014 | Banu et al. |
| 2015/0083384 A1 | 3/2015 | Lewis, Jr. et al. |
| 2015/0120067 A1* | 4/2015 | Wing ................... G05D 16/20 700/282 |
| 2015/0276268 A1 | 10/2015 | Hazzard et al. |
| 2015/0277463 A1 | 10/2015 | Hazzard et al. |
| 2015/0354833 A1 | 12/2015 | Kreutzman |

FOREIGN PATENT DOCUMENTS

| | | |
|---|---|---|
| CN | 201909441 | 7/2011 |
| CN | 102213489 | 10/2011 |
| CN | 203203717 | 9/2013 |
| EP | 0356609 | 3/1990 |
| EP | 0531072 | 3/1993 |
| EP | 0699316 | 7/1999 |
| EP | 0967440 A2 | 12/1999 |
| EP | 1148298 B1 | 10/2004 |
| EP | 1621814 | 2/2006 |
| EP | 1178748 | 10/2006 |
| EP | 2108140 | 6/2012 |
| FR | 2820206 | 8/2002 |
| GB | 2211331 | 6/1999 |
| JP | H 08264469 | 10/1996 |
| JP | 2005283039 | 10/2005 |
| JP | 2006084322 | 3/2006 |
| JP | 2008008548 | 1/2008 |
| JP | 2011220560 | 11/2011 |
| TW | 1431223 | 3/2014 |
| WO | 9718417 A1 | 5/1997 |
| WO | WO 2008/102263 | 8/2008 |
| WO | WO 2009/022226 | 2/2009 |
| WO | WO 2009/061622 | 5/2009 |
| WO | WO 2011/104592 | 9/2011 |

OTHER PUBLICATIONS

AO Smith, "IComm Remote Monitoring System, Instruction Manual," 64 pages, Jun. 2009.
U.S. Appl. No. 14/689,896, filed Apr. 17, 2015.
U.S. Appl. No. 14/964,392, filed Dec. 9, 2015.
U.S. Appl. No. 15/166,110, filed May 26, 2016.
Filibeli et al., "Embedded Web Server-Based Home Appliance Networks," Journal of Network and Computer Applications, vol. 30, pp. 499-514, 2007.
Halfbakery.com, "Hot Water Alarm," 2 pages, Sep. 4, 2002.
Heat Transfer Products Inc., "Specification for Heat Transfer Products, Inc., Vision 3 System," 2 pages, Mar. 17, 2006.
Hiller, "Dual-Tank Water Heating System Options," ASHRAE Transactions: Symposia, pp. 1028-1037, Downloaded Nov. 16, 2012.
Honeywell International Inc., "CS8800 General Assembly, Drawing Number 50000855," 2 pages, Oct. 24, 2008.
Honeywell International Inc., "Thermopile Assembly, Drawing Number 50006821," 1 page, Jun. 18, 2010.
Honeywell International Inc., "Thermopile Element, Drawing Number 50010166," 1 page, Apr. 1, 2005.
Honeywell International Inc., "Thermopile General Assembly, Drawing Number 50006914," 1 page, Jan. 12, 2006.
Honeywell International Inc., Photograph of a CS8800 Thermocouple Assembly, 1 page, saved Oct. 9, 2014.
http://nachi.org/forum/f22/dual-water-heater-installations-36034/, "Dual Water Heater Installation," 10 pages, printed Oct. 1, 2012.
http://www.whirlpoolwaterheaters.com/learn_more/energysmartelectricwaterheateroperation.aspx, link no longer functions, "Energy Smart Electric Water Heater Operation," 3 pages, prior to Nov. 13, 2012.
http://www.whirlpoolwaterheaters.com/learn-more/eletric-water-heaters/6th-sense%E2% . . . , "Whirlpool Energy Smart Electric Water Heater, Learn More," 3 pages, printed Jan. 15, 2015.
Industrial Controls, "Basics of PID Control (Proportional+Integral+Derivative)," downloaded from https://web.archive.org/web/20110206195004/http://wwww.industrialcontrolsonline.com/training/online/basics-pid-control-proportionalintegralderivative, 4 pages, Feb. 6, 2011.
InspectAPedia, "Guide to Alternative Hot Water Sources," 6 pages, printed Oct. 1, 2012.
Johnson Controls, "K Series BASO Thermocouples, Heating Line Product Guide 435.0, Thermocouples Section, Product Bulletin K Series," 8 pages, Oct. 1998.
Lennox, "Network Control Panel, User's Manual," 18 pages, Nov. 1999.
Moog, "M3000 Control System, RTEMP 8, Remote 8-Channel Temperature Controller with CanOpen Interface," 6 pages, Nov. 2004.
Process Technology, "Troubleshooting Electric Immersion Heaters," downloaded from http://www.processtechnology.com/troubleshootheaters.html, 3 pages, Mar. 22, 2010.

(56) References Cited

OTHER PUBLICATIONS

Raychem, "HWAT-ECO," Tyco Thermal Control, 4 pages, 2012.
Techno Mix, "Installation-Series and Parallel," downloaded from www.chinawinds.co.uk/diy_tips/installation_series_and_parallel.html, 5 pages, printed Oct. 1, 2012.
Triangle Tube, "Prestige Solo Condensing High Efficiency Gas Boiler," 4 pages, revised Apr. 30, 2012.
Reliance Water Heaters, "Service Handbook for Standard Residential FVIR Gas Water Heaters, Models: G/LORT, G/LORS, G/LBRT, G/LBRS/ G/LBCT, G/LBCS, G/LKRT, G/LKRS, G/LKCT, G/LART, G/LARS, G/LXRT, GLQRT—Series 200/201 and Series 202/203," 44 pages, Nov. 2009.

* cited by examiner

WATER HEATER LEAK DETECTION SYSTEM

This application claims the benefit of U.S. Provisional Application Ser. No. 62/128,956, filed Mar. 5, 2015, and entitled "Water Heater Leak Detection System". U.S. Provisional Application Ser. No. 62/128,956, filed Mar. 5, 2015, is hereby incorporated by reference.

BACKGROUND

The present disclosure pertains to detectors and particularly to leak detectors.

SUMMARY

The disclosure reveals a system for detecting moisture or water in a particular location. The system may incorporate a moisture detector having a control module, a moisture detection circuit connected to the control module, and a voltage source connected to the moisture detection circuit and to the control module. The voltage source and the moisture detection circuit may provide a voltage level to the control module when the moisture detection circuit detects dry condition. Another voltage level may go to the to the control module when the moisture detection circuit detects a wet condition. Still another voltage level may go to the control module when the moisture detection circuit detects a condition between the dry condition and the wet condition. A voltage level to the control module may indicate whether an appliance, such as a water heater, a washing machine, or a dish washer, which the control module controls, has a leak. If the leak is deemed by a voltage level from the circuit to be worthy of concern, then a display, an alarm, a message, or other notice may indicate an issue or what action needs to be taken.

DESCRIPTION

Figure 1:
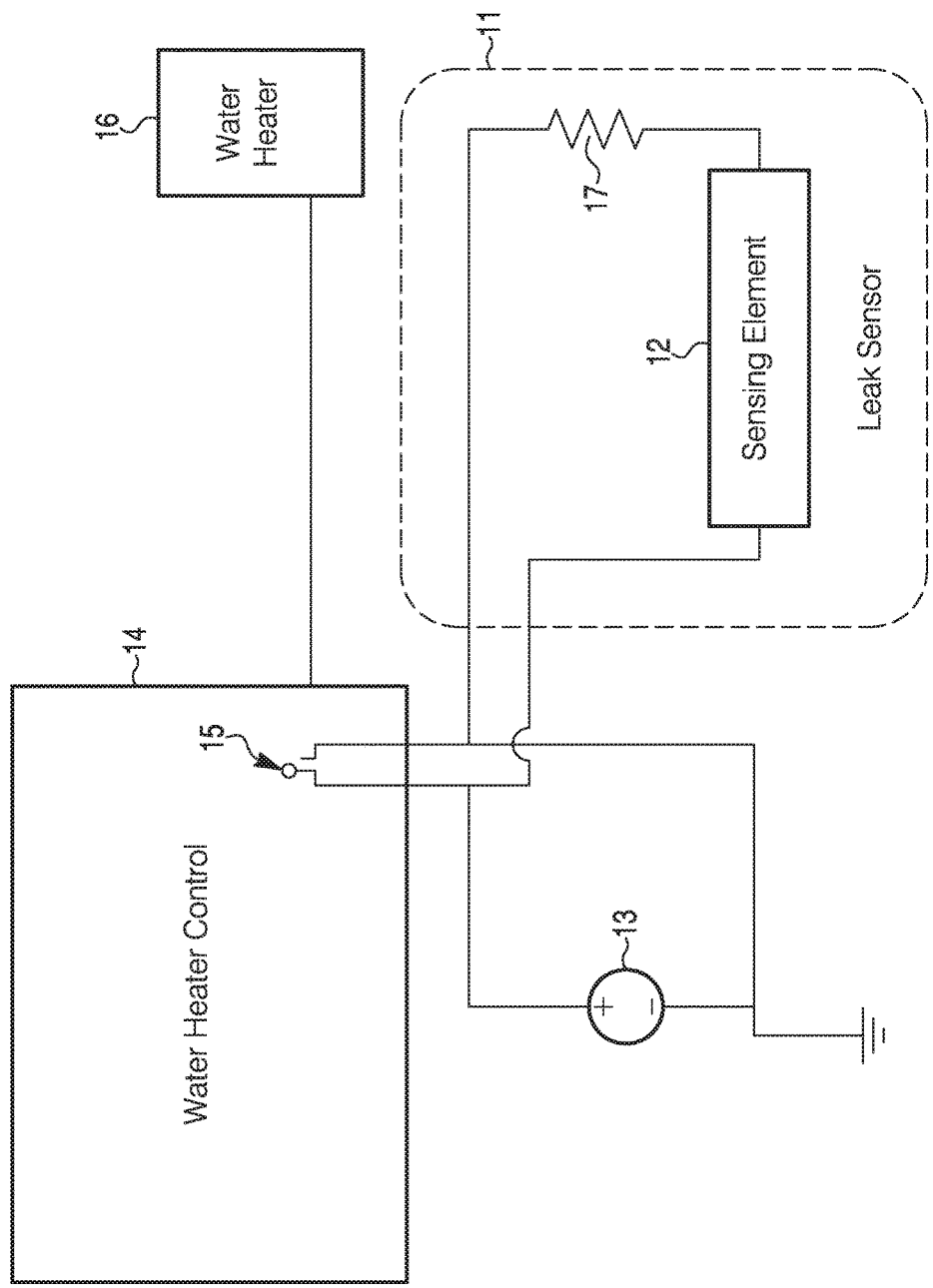
FIG. 1 is a diagram of a circuit for water leak detection.

The present system and approach may incorporate one or more processors, computers, controllers, user interfaces, wireless and/or wire connections, and/or the like, in an implementation described and/or shown herein.

This description may provide one or more illustrative and specific examples or ways of implementing the present system and approach. There may be numerous other examples or ways of implementing the system and approach.

Water heaters, or other water utilizing types of appliances, may have a natural risk of leaking and causing water damage to property. A water heater may be used as an illustrative example incorporating the present system and approach. A leak may not necessarily be noticed by a home owner until the damage has already occurred. An approach of detecting and alerting the home owner to a leak appears to be needed.

The present system may locate a sensor on the floor at the base of a water heater where any leaking water would first begin to pool. The sensor may be connected to thermopile voltage input. When the sensor is dry, it may have a large resistance and essentially be an open circuit. When the sensor becomes wet, its resistance may decrease. The decreased resistance may represent a current load to the thermopile and draw down the voltage available to the water heater control. Design of the sensor's resistance may allow the voltage to the control to be reduced either 1) just enough to be reliably detected by the control, or 2) enough to shut down the control.

In the first case, the control's software may recognize the detection of a leak through a fairly rapid and sustained decrease in thermopile voltage and then may take action such as going into a pilot only mode and flashing an error code. This may allow the water to have some level of warmth, but it may be cool enough that the home owner may likely investigate it very soon, discover the leak and the flashing error code, and take action to prevent damage to the home. The home owner may also reset the control, possibly by turning the control knob, to have the water heater start functioning again. The controller may then go into a mode that recognizes the leak, but allows the water heater to function for a period of time, possibly a week, without flagging another error. This may be beneficial if the leak is not going to cause damage because the home owner may continue to use the water heater until such time as it could be replaced or repaired.

The second case may be useful for an upgrade to controls that do not necessarily have software to respond to the sensor, such as the Vesta™ controls that may be currently installed in homes. The sensor may reduce the voltage available to the control enough so that the control would shut down. The water may become cold, so the home owner would again investigate and discover the leak. Cold water is undesirable, but not necessarily nearly as undesirable as water damage to one's home. The disadvantages of this system compared to the first may be 1) there would be no flashing error code to communicate the leak to the home owner, so if the leak were not obvious, the home owner may be confused as to why the controller shut down, 2) the water may become cold, not just cool or moderately warm, and 3)

the only way to allow the control to turn back on so the heater could be used may be to either move the sensor out of the water or to remove the sensor altogether. One recommendation may be to position the sensor in easy view so the first disadvantage would not necessarily be an issue.

The sensor may be made of a material that would have a very high electrical resistance when it is dry and would be a good electrical conductor when it is wet. A fixed resistor may likely be wired in series with this sensor and its value chosen to provide a voltage reduction as described herein. The two leads may then be connected at the same location as the thermopile connection on the water heater control so that it is in parallel with the thermopile.

The sensor material may be made from a number of compounds. Such a compound may need to be easily partially dissolved and ionized by water, which would allow it to conduct, such as a salt. The material may be such that it would not necessarily become entirely liquid or would be contained in a way that would prevent the material from leaking out of the sensor. The material may be made so it would never leak out of the sensor, but it may be acceptable to allow it to leak at a slow rate so the sensor will function for a limited period of time after it becomes wet. If the material could leak out, the sensor may effectively be a onetime-use sensor; but if the water heater is leaking, that may be probably ok. The material should be in a container that will allow the water in.

An alternate construction for the sensor may be having two wires forming a gap and using water between them as a conductor. Such an approach may be very inexpensive, but may also be dependent on the ion content of the water to reduce its resistance.

The sensor may be connected to an electrical input connector on the water heater (WH) control. The sensor may provide a specified electrical signal to this input when dry, most likely a large resistance, and a different signal when wet, most likely a low resistance. When the sensor becomes wet, the water heater control may recognize this condition and perform certain actions to alert the home owner. Such actions may include, but would not necessarily be limited to, 1) sounding an audible alarm, 2) putting the water heater control in a pilot only mode or idle mode, or reducing the temperature set point to significantly reduce the water temperature or change an operating level, 3) flashing an error code, and/or 4) sending an electronic message.

The sensor may use any type of electrical signal, could be passive (unpowered) or active (powered), but may most likely be resistive. If the sensor is resistive, it may essentially be an open circuit when dry, and essentially be a short circuit when wet.

The sensor may be made of a material that would have a very high electrical resistance when it is dry and would be a good electrical conductor when it is wet. A fixed resistor may likely be wired in series with this sensor and its value chosen to provide a voltage reduction as described herein. The two leads may then be connected at the same location as the thermopile connection on the water heater control so that it is in parallel with the thermopile.

The sensor material may be made from a number of compounds. Such a compound may need to be easily partially dissolved and ionized by water, which may allow it to conduct, such as a salt. The material may be such that it would not necessarily become entirely liquid or would be contained in a way that would prevent the material from leaking out of the sensor. The material may be made so it would never leak out of the sensor, but it may be acceptable to allow it to leak at a slow rate so the sensor will function for a limited period of time after it becomes wet. If the material could leak out, the sensor may effectively be a onetime-use sensor, but if the water heater is leaking, that may be probably ok. The material should be in a container that will allow the water in.

An alternate construction for the sensor may be having two wires forming a gap and using water between them as a conductor. Such an approach may be rather inexpensive, but would also be dependent on the ion content of the water to reduce its resistance.

The water heater control may be upgraded from current designs to include a small, but loud alarm speaker. Such a speaker may be applied to water heater controls that are powered from wall power, 24V volts, or thermopiles. In wall powered or 24V systems, the speaker may be driven directly and provide pretty much any sound desired, using digital sound generating or transformation circuitry. In thermopile powered systems, the control may include some type of power storage system such as a battery or a super capacitor to provide power to drive the speaker. A capacitor circuit may take excess power from the thermopile to charge the super cap and provide the audible alarm whenever the super cap had sufficient power to do so. Such an audible alarm may most likely have to be a short, loud, high frequency noise sounded periodically. The speaker may be any type of speaker, but the lower the power consumption the better, at least for thermopile powered controls.

FIG. 1 is a diagram of a circuit for water leak detection. A leak sensor 11 may be situated in an area where water from a water heater or other appliances may gather if the heater or other appliance is to spring a leak, even if very small. Leak sensor 11 may contain a sensing element 12 that may have a very large resistance when it is dry. The sensing element may have a significantly lower resistance when it becomes moist or wet. A thermopile 13 may provide a voltage to a water heater 16 control module 14 for its operation at a connection 15. Leak sensor may be connected in parallel with thermopile 13. If sensing element becomes moist or wet, then a significant load may be applied to thermopile 13 which reduces its output. The lower output voltage to heater control module 14 may result in a shutdown of control module 14 and in turn water heater 16 controlled by control module 14, a reduction in operation of water heater 16, or other action relative to control module 14 and water heater 16. Resistor 17 may be connected in series with one of the connections of sensing element 12 to adjust the effect of sensing element 12 on thermopile 13.

Figure 2:
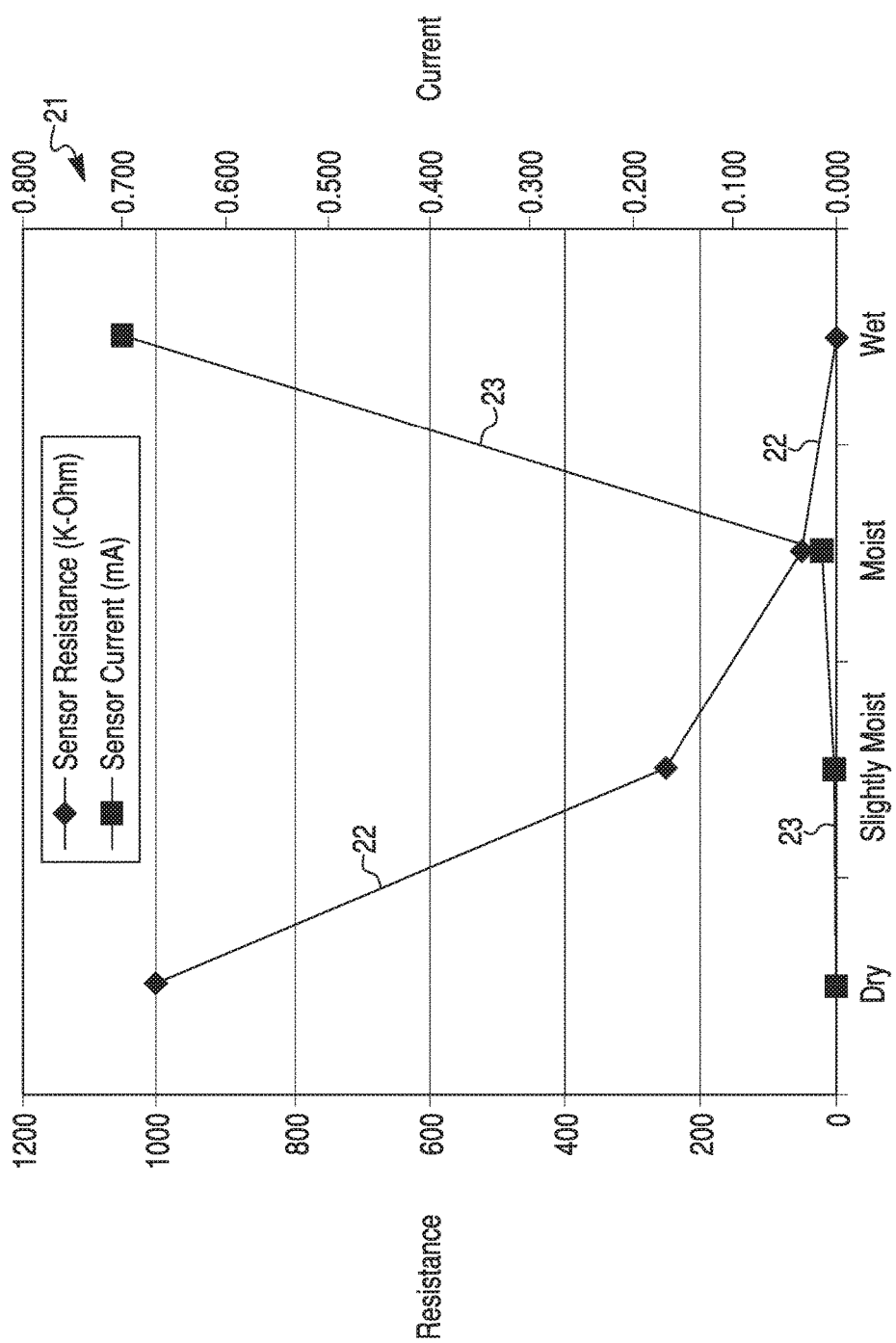
FIG. 2 is a diagram that reveals a graph showing an effect of moisture on a material used in a sensing element.

FIG. 2 is a diagram that reveals a graph 21 showing an effect of moisture on a material used in sensing element 12. Curve 22 is a plot of resistance of sensing element 12 in terms of K-ohms versus dry to wet conditions of the material. Curve 23 is a plot of current flow in sensing element 12 in terms of milliamps versus dry to wet conditions of the material.

Figure 3:
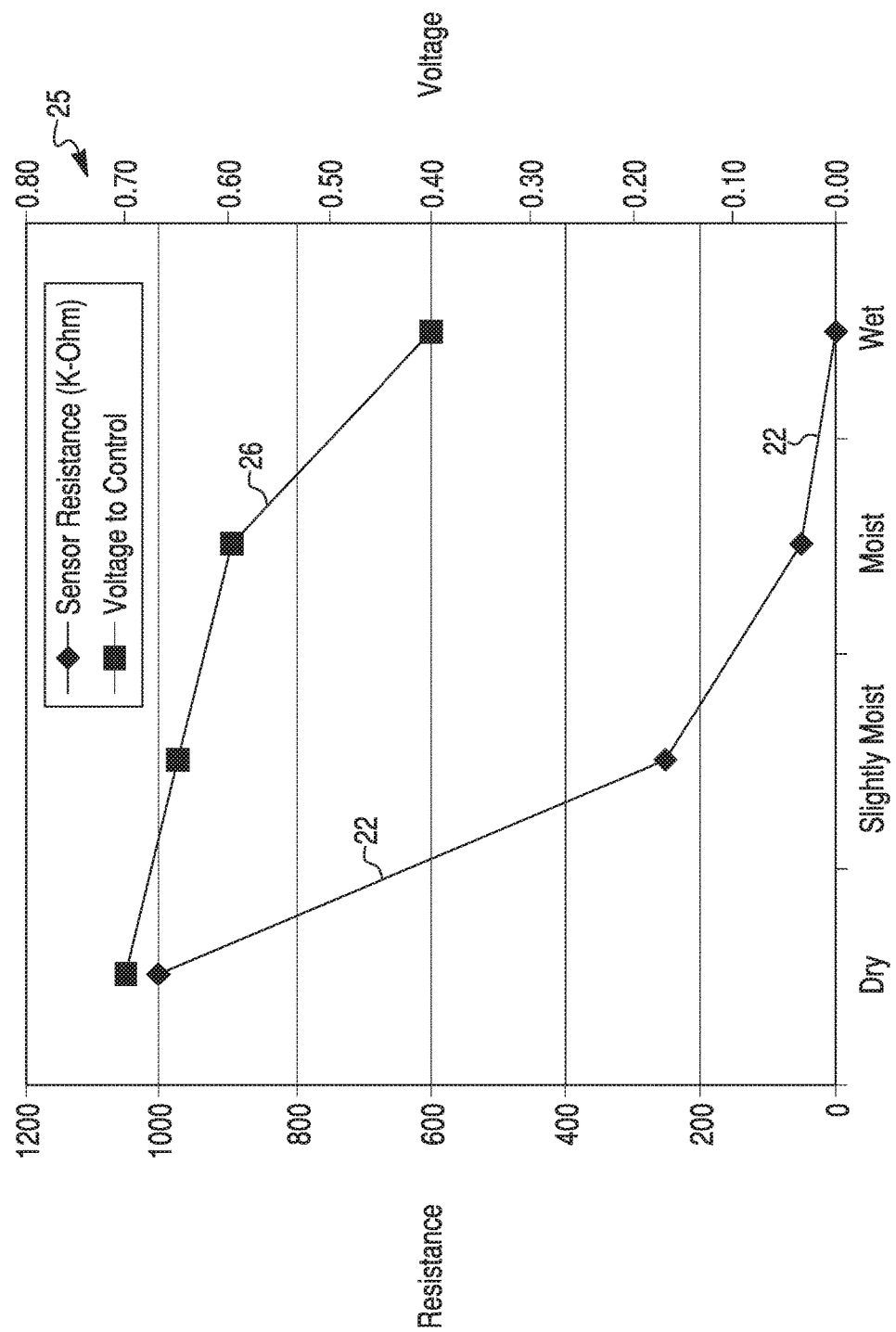
FIG. 3 is another diagram that reveals a graph showing an effect of moisture on the material used in a sensing element.

FIG. 3 is another diagram that reveals a graph 25 showing an effect of moisture on the material used in sensing element 12. Curve 22 is a plot of current flow in sensing element 12 versus dry to wet conditions like that of curve 22 in graph 21 of FIG. 2. A curve 26 is a plot of voltage provided at connection 15 to heater control module 14 versus dry to wet conditions.

Figure 4:
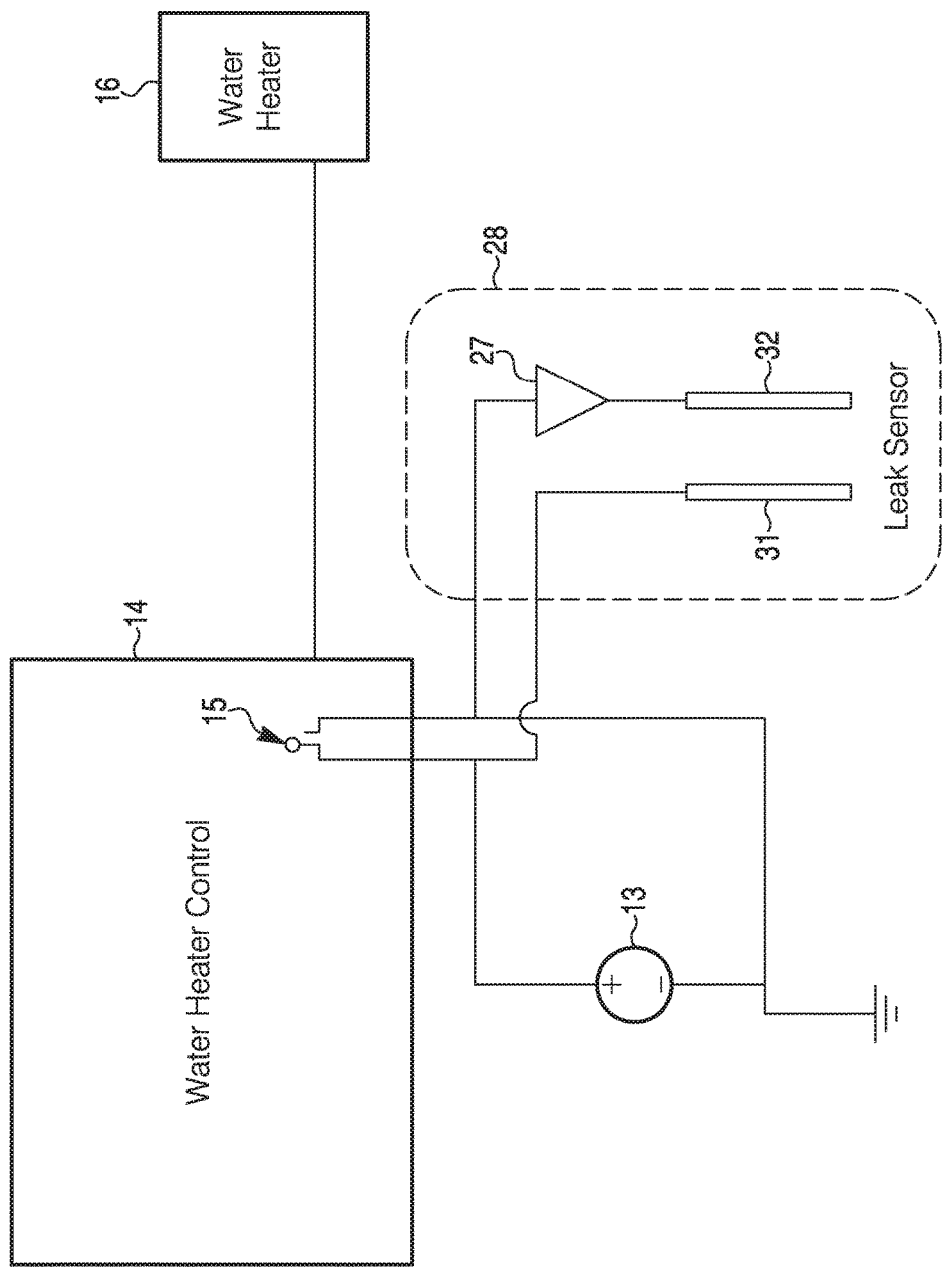
FIG. 4 is a diagram of another circuit used in lieu of the circuit of FIG. 1, for water leak detection.

FIG. 4 is a diagram of another circuit in lieu of the circuit of FIG. 1, for water leak detection. A leak sensor 28 may be used in lieu of leak sensor 11. Leak sensor 28 may have two leads, wires or probes 31 and 32 having a gap between them and using water as a conductor to short out the gap. Sensor 28 may use a signal amplifier 27 to detect the current between the two wires/conductors. Amplifier 27 may be incorporated in sensor 28 or in water heater control module 14.

Figure 5:
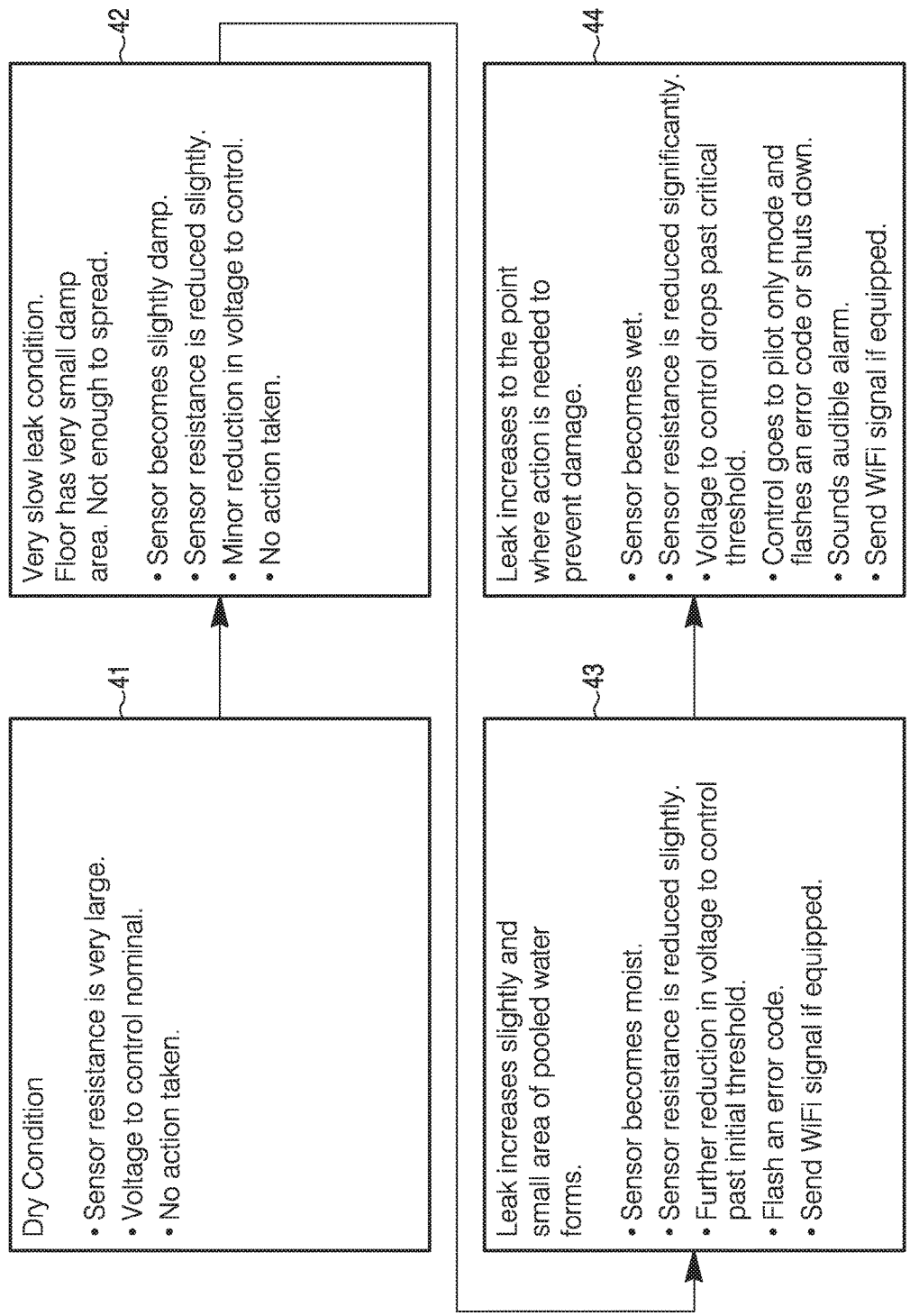
FIG. 5 is a diagram of blocks or symbols illustrating the various conditions from dry to wet on a leak sensor.

FIG. 5 is a diagram of blocks or symbols illustrating the various conditions from dry to wet on a leak sensor. Symbol 41 may indicate a dry condition around a water heater. Here, sensor resistance may be very large. Voltage to a water heater control module may be nominal. No action is necessarily needed by the control module.

A symbol 42 may indicate a very slow leak condition of the water heater. The floor around may have a very small damp area near the heater but not enough to spread. The leak sensor may become slightly damp and the sensor resistance may be reduced slightly. The voltage to the heater control module may incur a minor reduction. Action relative to the slightly damp condition is not necessarily taken.

A symbol 43 may indicate a leak that may increase slightly resulting in a small area of pooled water that forms. The leak sensor may become moist with the sensor resistance reduced slightly. A further reduction in voltage to the heater control module may be past an initial threshold. This situation may result in a flash of an error code. A Wi-Fi signal may be sent if equipped.

In symbol 44, a leak may be revealed to increase to a point where action is needed to prevent damage. The leak sensor may become wet and the sensor resistance may be reduced significantly. A voltage to the heater control module may drop past a critical threshold. The heater control module may go into a pilot only mode and flash an error code, or the module may shut down. An audible alarm may be sounded. A Wi-Fi signal may be sent if equipped. For the case described in symbol 44, it may also be that the sensor responds like a switch, going from high resistance or open circuit to low resistance or closed circuit essentially instantly. Basically, the sensor may detect water to some threshold, then indicate it as a leak. Until that point, the sensor has necessarily no effect on a leak detection system.

Figure 6:
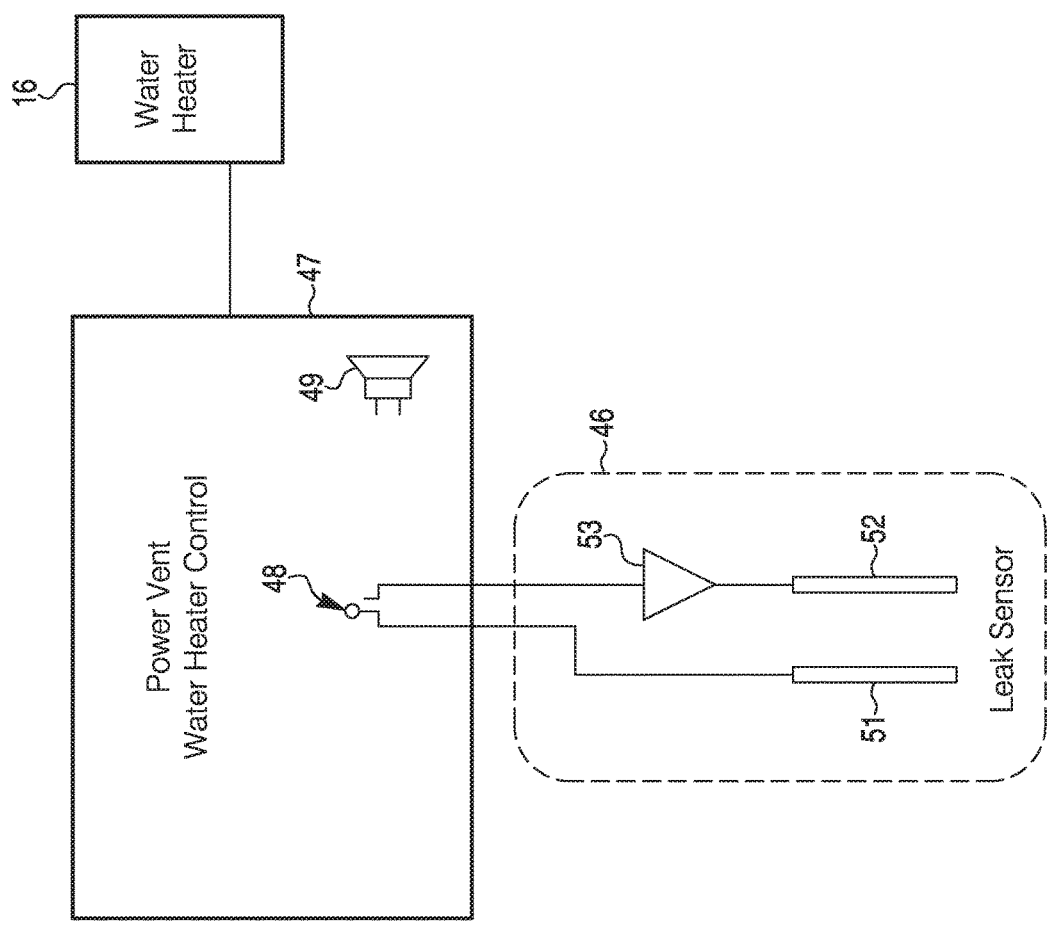
FIG. 6 is a diagram of a leak sensor similar to the leak sensor of FIG. 4 but not connected across the terminals of a voltage source.

FIG. 6 is a diagram of a leak sensor 46 similar to leak sensor 28 of FIG. 4 but not connected across the terminals of a thermopile voltage source 13. Leak sensor 46 may be connected to a water heater control with an external power source, for example 24 VAC or line voltage, such as a Power Vent water heater control. Leak sensor 46 may have water heater control module 47 via a dedicated connection or an RS232 connection 48, among other types of connections. Control module 47 may have a speaker 49 for alarms, notices, announcements, and the like. Speaker 49 may also or instead be incorporated in leak sensor 46. Leak sensor 46 may have leads, electrodes or bare wire ends 51 and 52 at a floor surface near a water heater that is being monitored for leaks. Sensor 28 may use a signal amplifier 53 to better detect a current between the two wires or conductors. Amplifier 27 may be incorporated in sensor 46 or in water heater control module 47.

Figure 7:
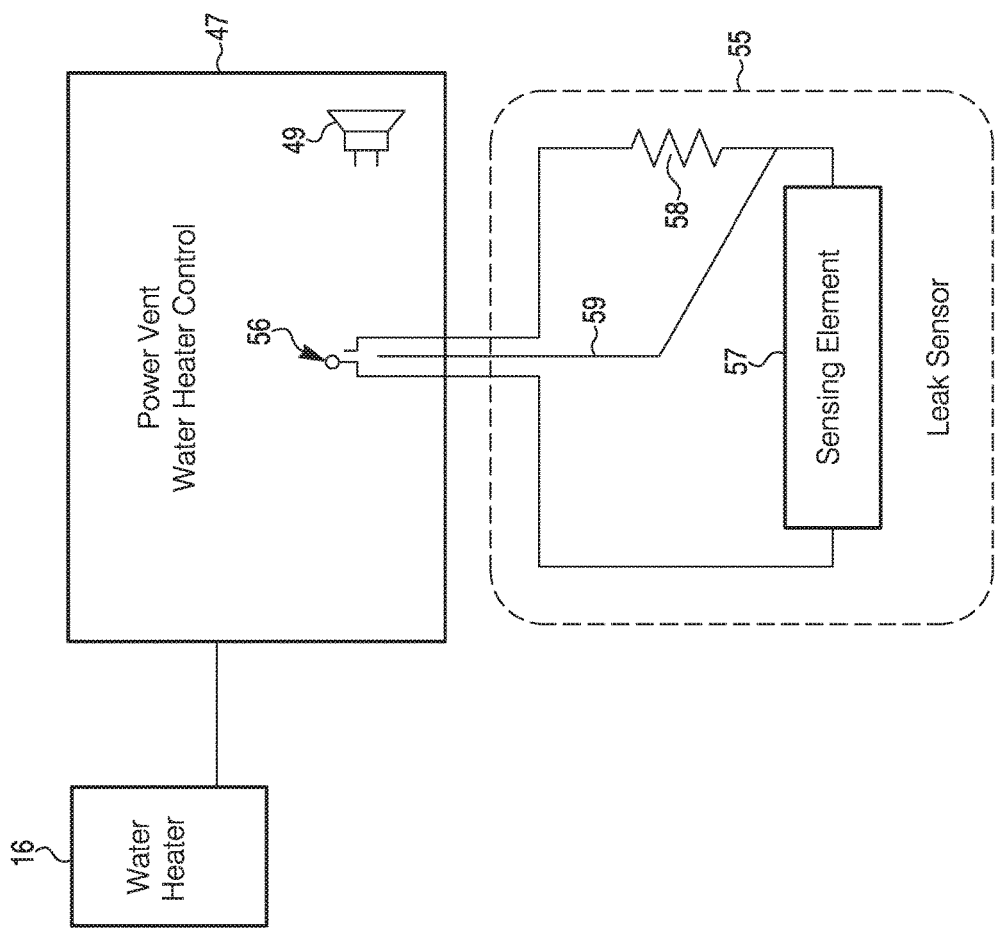
FIG. 7 is a diagram of a leak sensor similar to the leak sensor of FIG. 1 but not connected across the terminals of a voltage source.

FIG. 7 is a diagram of a leak sensor 55 similar to leak sensor 11 of FIG. 1 but not connected across the terminals of a thermopile voltage source 13. The connection from leak sensor 55 to control module 47 may be dedicated. Various other kinds of connections may be incorporated as a connection 56. Leak sensor 55 may have a sensing element 57 that detects dry, damp, moist and wet conditions. Sensing element 57 may contain a material like that of sensing element 12 of FIG. 2. Characteristics of the material are illustrated in the graphs 21 and 25 of FIG. 2 and FIG. 3, respectively. A resistor 58 may be connected in series with one of the leads of sensing element 57 to connection 56 of heater control module 47. Heater control module 47 in FIG. 6 and FIG. 7 may be connected to a water heater 16. In the configuration of FIG. 7, it may be advantageous for refined detection to have a connection 59 between sensing element 57 and resistor 58 to sense a voltage at that point. Connection 59 may be optional.

Figure 8:
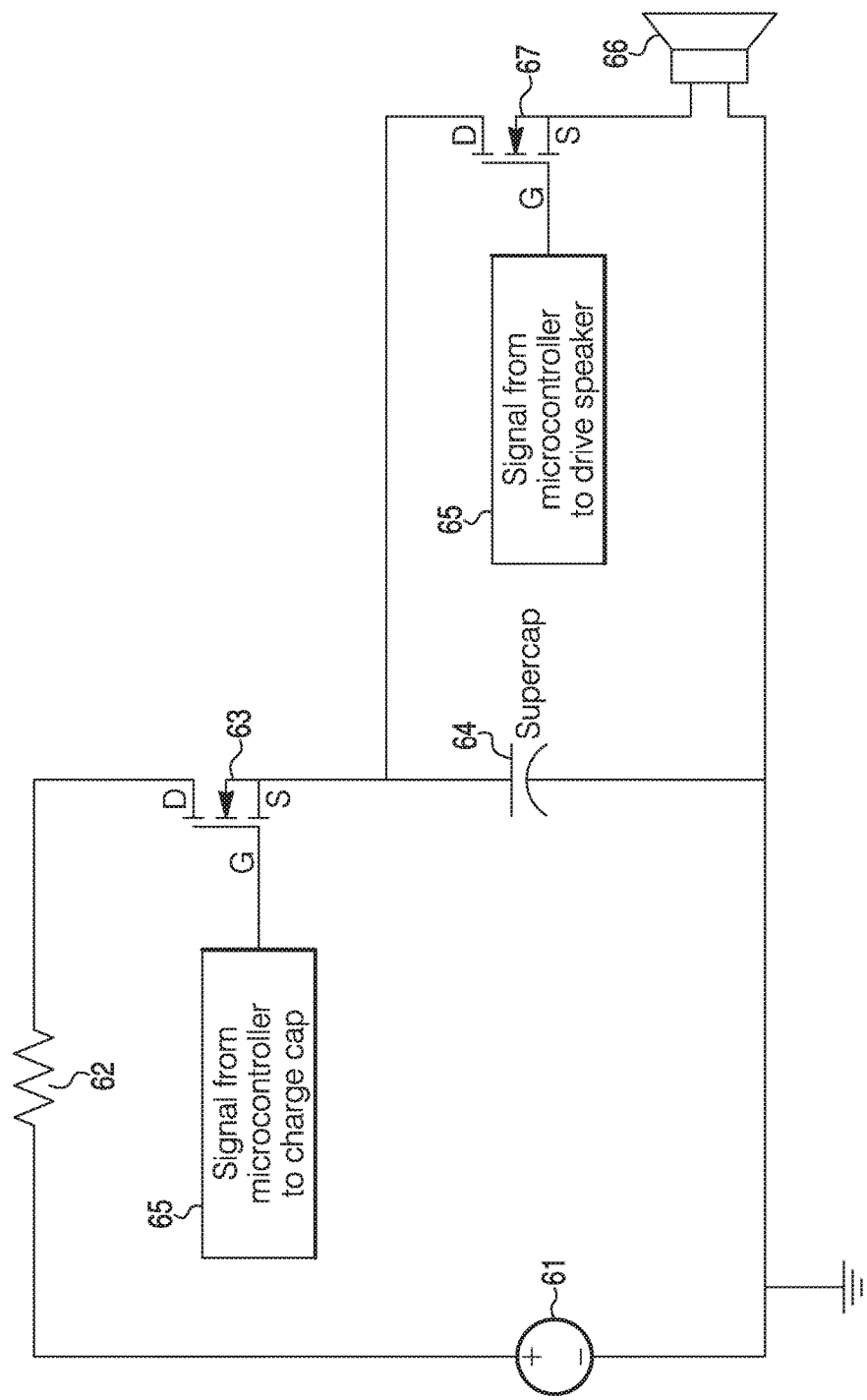
FIG. 8 is a diagram of an alarm speaker power circuit for leak detection systems of FIG. 6 and FIG. 7.

FIG. 8 is a diagram of an alarm speaker power circuit for leak detection systems of FIG. 6 and FIG. 7. A thermopile 61 may have one terminal connected to a current limiting resistor 62. The other end of resistor 62 may be connected to a drain-terminal of an N-channel MOSFET 63. A source terminal of FET 63 may be connected to a first electrode of a super capacitor 64. The second electrode of capacitor 64 may be connected to another terminal of thermopile 61. A microcontroller 65 may provide a signal to a gate of FET 63 to control an amount of current from thermopile 61 to charge capacitor 64. Super capacitor 64 may be charged from excess thermopile power and stored for used by a speaker 66. One terminal of speaker 66 may be connected to the second electrode of capacitor 64. The other terminal of speaker 66 may be connected to a source of an N-channel MOSFET 67. A drain of FET 67 may be connected to the first electrode of capacitor 64. FET 67 may control an amount of current from super capacitor 65 to speaker with a signal from microcontroller 65 to a gate of FET 67. A current control component may incorporate another kind of electronic device besides a FET. The power or voltage source may be another kind of device besides a thermopile.

Figure 9:
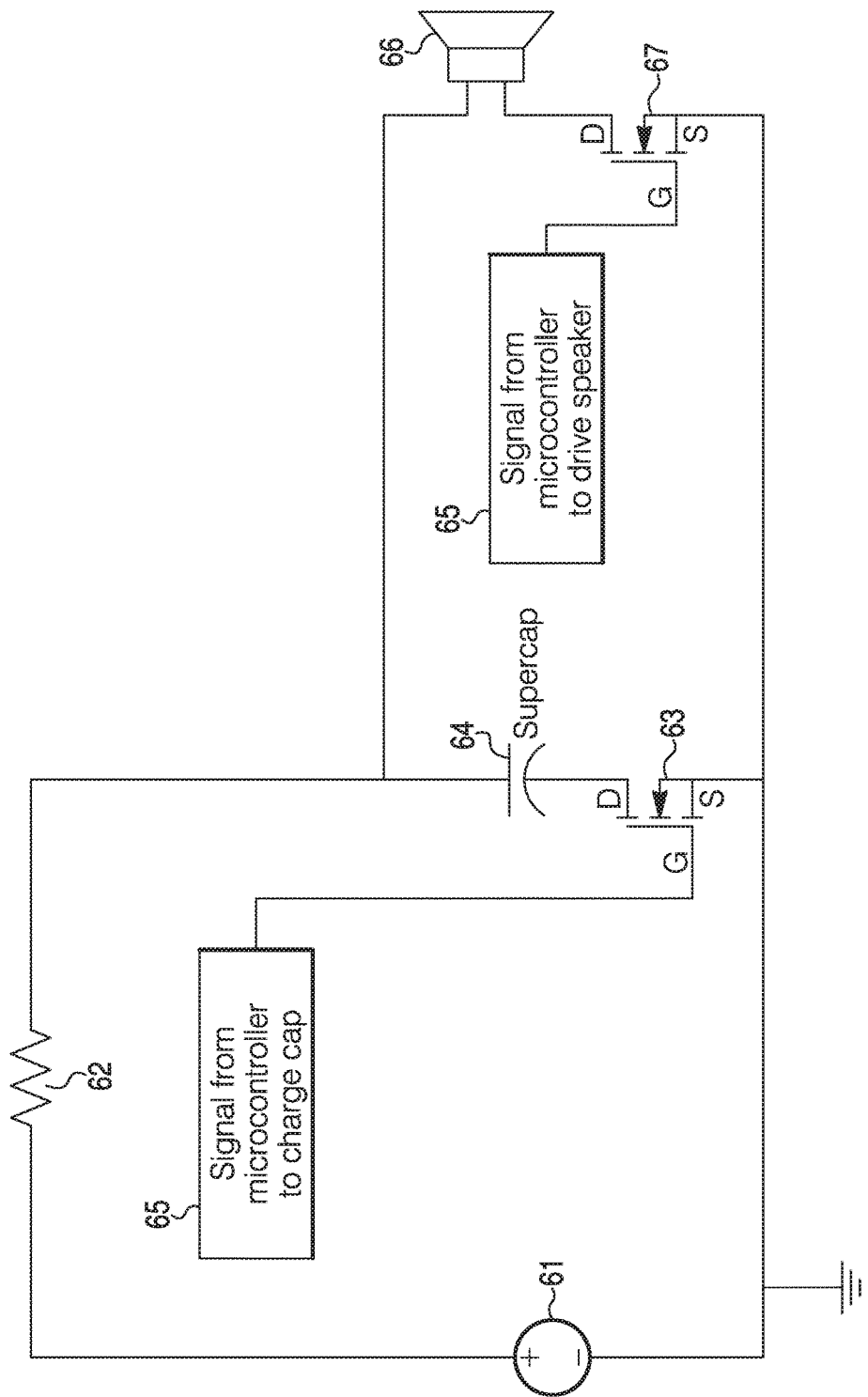
FIG. 9 is a diagram of another version of the alarm speaker power circuit shown in FIG. 8.

FIG. 9 is a diagram where FET 63 may instead be connected below the super cap 64. Speaker 66 may be placed above the FET item 67. One terminal of voltage source 61 may be connected to one end of current limiting resistor 62 and another terminal connected to a source of FET 63 and a source of FET 67. The other end of resistor 62 may be connected to a first electrode of super capacitor 64 and to a terminal of speaker 66. A second electrode of capacitor 64 may be connected to a drain of FET 63. A signal from microcontroller 65 to charge up capacitor 64 may go along a line to FET 63. Another signal from microcontroller 65 to drive speaker 66 may go along a line to a gate of FET 67. Another terminal of speaker 66 may be connected to a drain of FET 67.

A power vent does not necessarily require the capacitor 64 circuit version for providing power to speaker 66. The power vent may drive speaker 66 directly in the systems shown by diagrams of FIG. 6 and FIG. 7.

Figure 10:
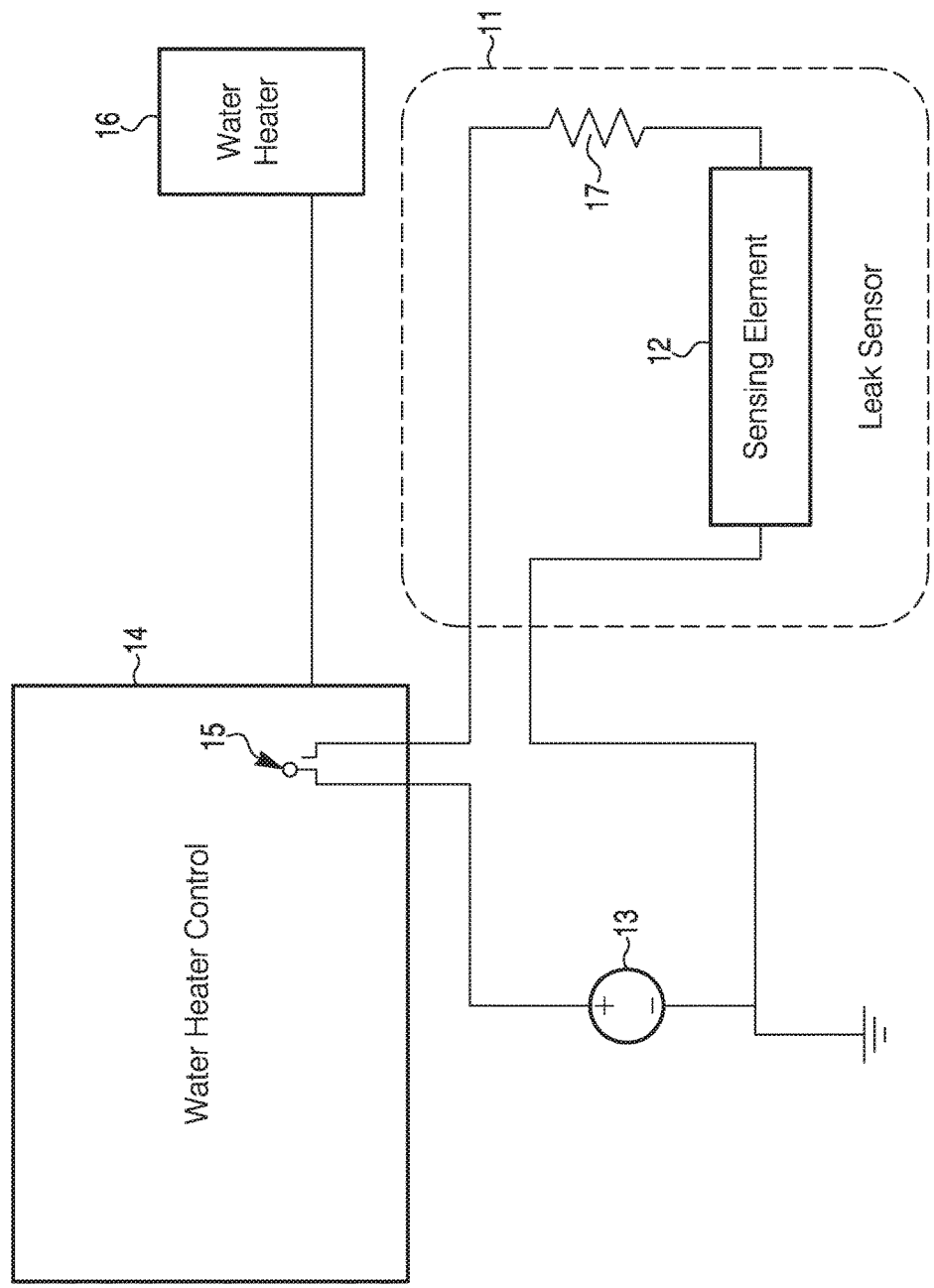
FIG. 10 is a diagram of another circuit for water leak detection that appears similar to but with some different connections from the circuit shown in FIG. 1.

FIG. 10 is a diagram of another circuit for water leak detection that appears similar to the circuit shown in FIG. 1. However, leak sensor 11 is connected in series with voltage source 13 in the circuit of FIG. 10 rather than in parallel as in the circuit of FIG. 1. In this case, the sensing element may be of low resistance or a closed circuit when dry and of high resistance or an open circuit when wet.

Figure 11:
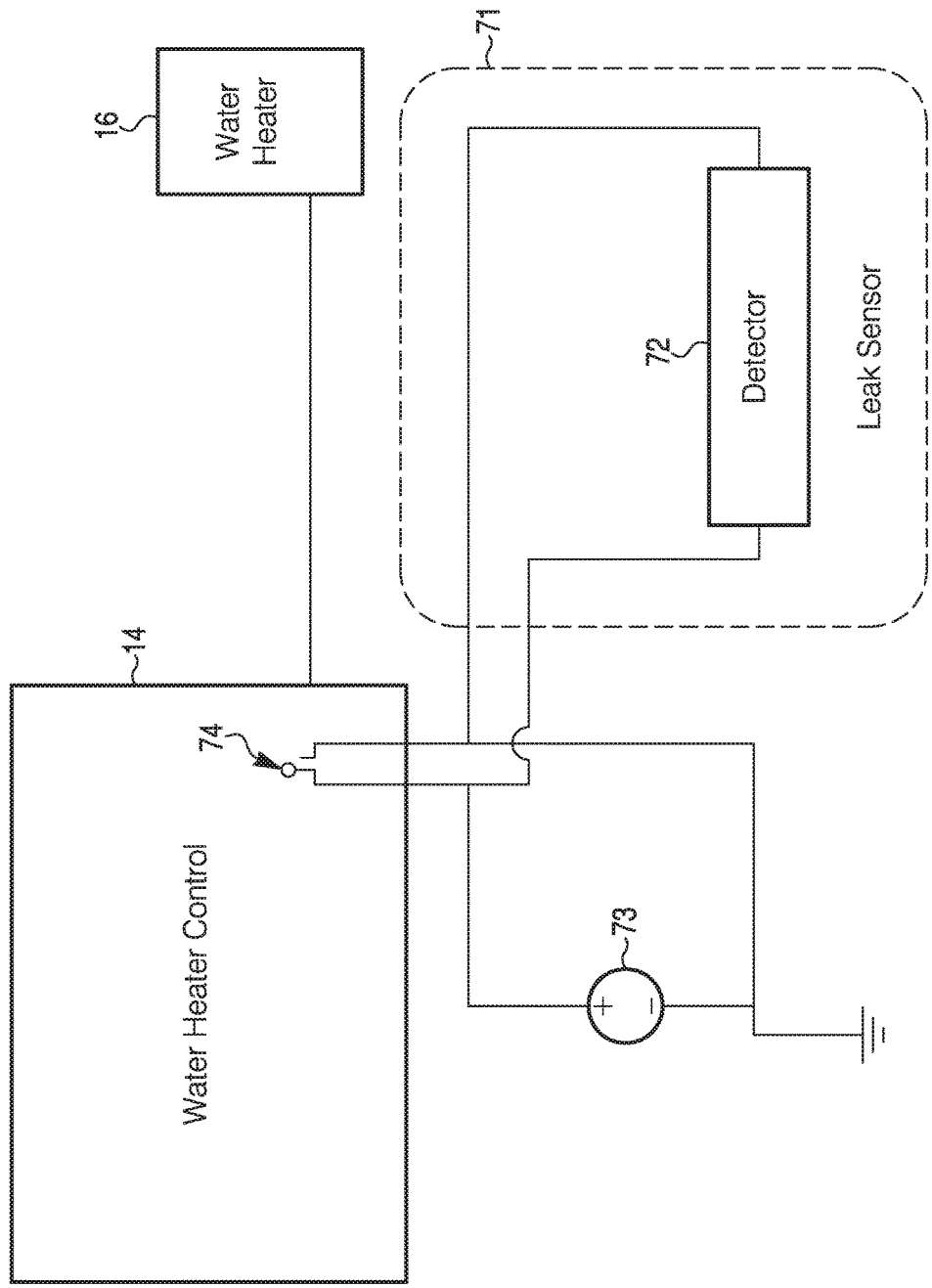
FIG. 11 is a diagram of a circuit for water leak detection that has a leak sensor utilizing a moisture, water, humidity or other kind of detector, different from the circuit of FIG. 1.

FIG. 11 is a diagram of a circuit for water leak detection system that has a leak sensor 71 utilizing a moisture, water or humidity or other kind of detector 72. Detector 72 may be a switch that indicates a presence of dryness and wetness with an open or closed switch. Leak sensor 71 may detect moisture in a manner different than that of leak sensors 11, 28, 46 and 55, of circuits in the diagrams of FIGS. 1 and 9, 4 and 10, 6, and 7, respectively. Leak sensor 71 may be constructed as a switch or other electrical mechanism that does not necessarily have a change in resistance in a presence of water from, for example, water heater 16. An indication of moisture or water may be indicated on a display, an audible alarm may sound, a light may flash, or a communication may be sent, and so forth. For an example of power for an indication, an alarm, a light, a communication, a display, and so on, may be powered by a thermopile, a super capacitor, a battery, or other source of power.

A connection 74 to water heater control module 14 may be a dedicated connection, an RS232 connection, a voltage source connection such as that of a thermopile, or some other kind of connection.

Figure 12:
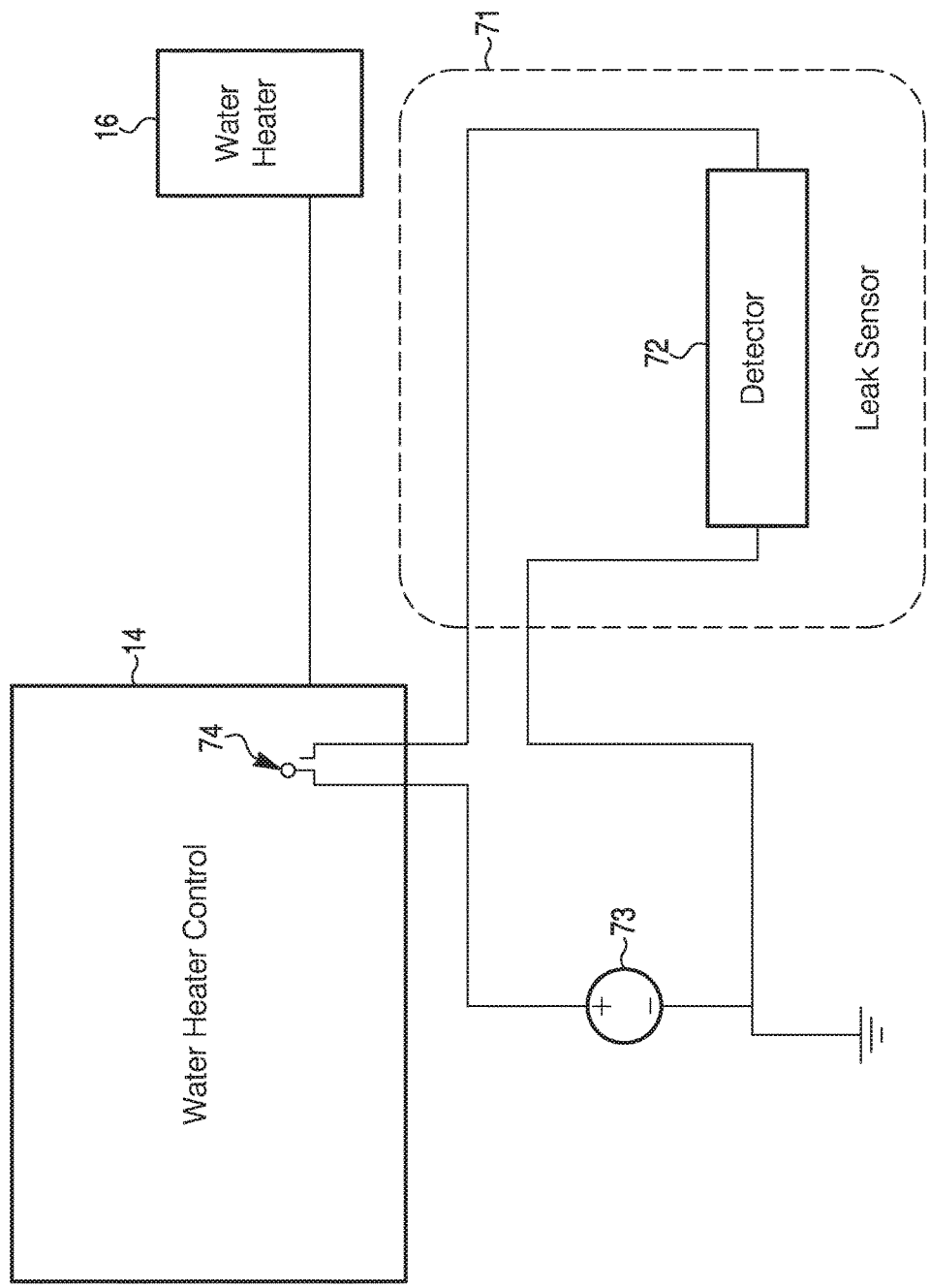
FIG. 12 is a diagram of a circuit for water leak detection that appears similar to but with some different connections from the circuit shown in FIG. 11.

FIG. 12 is a diagram of a circuit for a water leak detection system like that shown in the diagram of FIG. 11. One difference is that leak sensor 71 may instead be connected in series with source 73 rather than in parallel.

Figure 13:
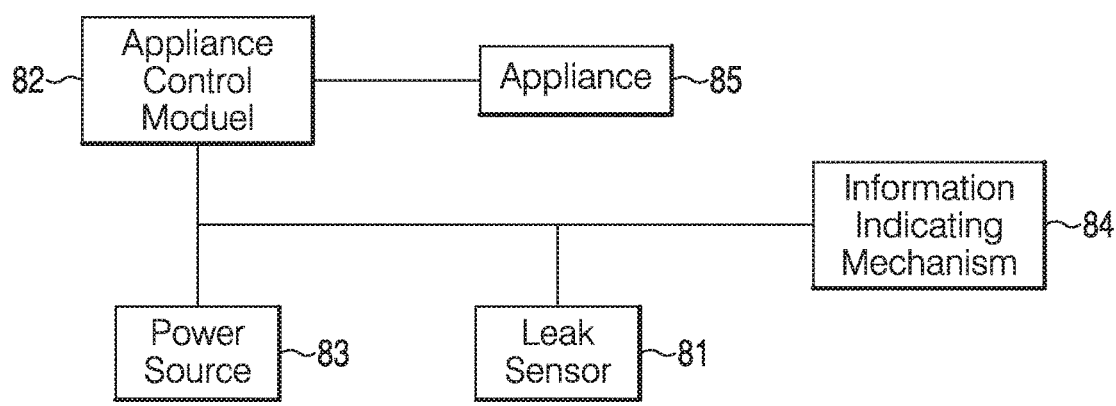
FIG. 13 is a diagram of water leak detection system for an appliance in general.

FIG. 13 is a diagram of water leak detection system for an appliance in general. A leak detector 81 may be connected to an appliance control module 82, a power source 83 and an information indicating mechanism 84. Appliance control module 82 may be connected to an appliance 85.

To recap, a moisture detector may incorporate a water heater control module, a moisture detection circuit connected to the water heater control module, and a voltage source connected to the moisture detection circuit and to the water heater control module. The voltage source and the moisture detection circuit may provide a first voltage level to the water heater control module when the moisture detection circuit detects a dry condition. The voltage source and the moisture detection circuit may provide a second voltage level to the water heater control module when the moisture detection circuit detects a wet condition. The voltage source and the moisture detection circuit may provide a third voltage level to the water heater control module when the moisture detection circuit detects a condition between the dry condition and the wet condition.

A voltage level to the water heater control module may indicate whether a water heater that the water heater control module controls, has a leak.

The second voltage level may indicate a condition of moisture that causes the water heater control module to reduce a water temperature set point of the water heater, flash an error code, or send an electronic message, to indicate a presence of moisture due to a leak in the water heater, or the second voltage level may indicate a wet condition that uses the water heater control module to go to a pilot light only mode for the water heater, flash an error code, shut down the water heater, sound an audible alarm, or send an electronic message, indicating that action is needed to prevent water damage.

When the third voltage level is at the first voltage level or the second voltage level, no action is necessarily needed relative to the water heater having a leak. When the third voltage level is at the second voltage level, action may be needed relative to the water heater having a leak.

The voltage source and the moisture detection circuit may be connected in series.

The voltage source and the moisture detection circuit may be connected in parallel.

The audible alarm may be powered by a super capacitor that is charged by power from the voltage source.

The moisture detection circuit may incorporate a sensing element that has a resistance that changes upon contact with moisture, or the moisture detection circuit may incorporate a sensing element that indicates contact with moisture without a change in resistance.

An approach for detection of a leak from a water heater may incorporate connecting a moisture detector to a control module for a water heater, and connecting a voltage source to the moisture detector. The moisture detector may have has a resistance that changes upon contact with moisture. Changes of the resistance of the moisture detector may change the voltage of the voltage source. Changes of the voltage of the voltage source may be detected by the control module and interpreted by the control module as a change in a level of moisture detected by the moisture detector. The moisture detector may be situated in a place where if the water heater has a leak, moisture from the leak would gather at the place.

The approach may further incorporate equating an amount of a change of voltage of the voltage source, detected by the control module to an amount of change of moisture detected by the moisture detector.

A first level of voltage may indicate a lack of moisture in the place where the moisture detector is situated. A second level of voltage may indicate wetness in the place where the moisture detector is situated. A third level of voltage may indicate a condition of moisture between a lack of moisture and wetness in the place where the moisture detector is situated.

The first level of voltage detected by the control module may result in no action needed relative to the water heater. The second level of voltage detected by the control module may result in going to a pilot light only mode for the water heater, flashing an error code, shutting down the water heater, sounding an audible alarm, or sending an electronic message, to indicate that action is needed to prevent or minimize water damage caused by a leak in the water heater.

The control module may be powered by the voltage source. The voltage source may be an item selected from a group incorporating thermopiles, line power, batteries, solar cells, charged super capacitors, and wind generators.

An appliance leak detection system may incorporate a leak sensor, a control module connected to an appliance, and a voltage source connected to the leak sensor and the control module. The appliance may be selected from a group incorporating a water heater, a dishwasher and a washing machine. The leak sensor may be located in an area where dampness or wetness would appear if the appliance had a leak, and would be sensed by the leak sensor.

The leak sensor may have a resistance of an open circuit when situated in an area of dryness, and have a resistance of a short circuit when situated in an area of wetness.

The leak sensor may be selected from a group of items incorporating non-discrete variable resistance moisture detectors, discrete variable resistance moisture detectors and moisture sensitive switches.

The leak sensor may have a resistance of a closed circuit when situated in an area of dryness, and have a resistance of an open circuit when situated in an area of wetness.

The leak sensor may have a resistance that changes according to an amount of dampness or wetness detected by the leak sensor. A magnitude of voltage from the voltage source may be present at the control module. When a resistance of the leak sensor changes, the magnitude of voltage present at the control module may change.

When the magnitude of voltage present at the control module changes, the control module may recognize a change of an amount of dampness or wetness detected by the leak sensor.

The amount of dampness or wetness detected by the leak sensor may vary from dry to wet.

A dry condition may indicate zero percent moisture and a wet condition may indicate one hundred percent moisture. A level one may be a dry condition. A level two may be a predetermined percent of moisture greater than zero percent. A level three may be a predetermined percentage of moisture greater than that of level two and less than one hundred percent moisture. A level four may be a wet condition.

At level one the control module may operate in a routine manner. At level two, the control module may operate in a routine manner. At level three the control module may flash an error code, change an operating level or reduce a water temperature set point of the appliance, or send a Wi-Fi signal to indicate a presence of moisture, or shut down the appliance and sound an audible alarm. At level four, the control module may go to an idle mode for the appliance, flash an error code, shut down the appliance, sound an audible alarm, or send a Wi-Fi signal indicating action is needed to prevent water damage.

The voltage source may be selected from a group incorporating thermopiles, line power, batteries, solar cells, charged super capacitors, and wind generators.

U.S. patent application Ser. No. 14/225,282, filed Mar. 25, 2014, is hereby incorporated by reference. U.S. patent application Ser. No. 14/225,308, filed Mar. 25, 2014, is hereby incorporated by reference.

Any publication or patent document noted herein is hereby incorporated by reference to the same extent as if each publication or patent document was specifically and individually indicated to be incorporated by reference.

In the present specification, some of the matter may be of a hypothetical or prophetic nature although stated in another manner or tense.

Although the present system and/or approach has been described with respect to at least one illustrative example, many variations and modifications will become apparent to those skilled in the art upon reading the specification. It is therefore the intention that the appended claims be interpreted as broadly as possible in view of the related art to include all such variations and modifications.

What is claimed is:

1. A moisture detector comprising:
   a water heater control module;
   a moisture detection circuit connected to the water heater control module; and
   a voltage source connected to the moisture detection circuit and to the water heater control module such that a voltage level provided to the water heater control module by the voltage source and the moisture detection circuit indicates whether a water heater that the water heater control module controls has a leak; and
   wherein:
   the voltage source and the moisture detection circuit provide a first voltage level to the water heater control module when the moisture detection circuit detects a dry condition;
   the voltage source and the moisture detection circuit provide a second voltage level to the water heater control module when the moisture detection circuit detects a wet condition;
   the voltage source and the moisture detection circuit provide a third voltage level to the water heater control module when the moisture detection circuit detects a condition between the dry condition and the wet condition;
   when the third voltage level is between the first voltage level and the second voltage level, no action is needed relative to the water heater having a leak; and
   when the third voltage level is at the second voltage level, action is needed relative to the water heater having a leak.

2. The detector of claim 1, wherein the second voltage level indicates a condition of moisture that causes the water heater control module to reduce a water temperature set point of the water heater, flash an error code, or send an electronic message, to indicate a presence of moisture due to a leak in the water heater; or the second voltage level indicates a wet condition that uses the water heater control module to go to a pilot light only mode for the water heater, flash an error code, shut down the water heater, sound an audible alarm, or send an electronic message, indicating that action is needed to prevent water damage.

3. The detector of claim 2, wherein the audible alarm is powered by a super capacitor that is charged by power from the voltage source.

4. The detector of claim 1, wherein the voltage source and the moisture detection circuit are connected in series.

5. The detector of claim 1, wherein the voltage source and the moisture detection circuit are connected in parallel.

6. The detector of claim 1, wherein the moisture detection circuit comprise a sensing element that has a resistance that changes upon contact with moisture; or the moisture detection circuit comprises a sensing element that indicates contact with moisture without a change in resistance.

7. A method for detection of a leak from a water heater comprising:
   connecting a moisture detector to a control module for a water heater;
   connecting a voltage source to the moisture detector; and
   indicating whether the water heater has a leak by providing a voltage level to the water heater control module from the moisture detector; and
   wherein:
   the moisture detector has a resistance that changes upon contact with moisture;
   changes of the resistance of the moisture detector change the voltage level provided to the water heater control module;
   changes of the voltage level provided to the water heater control module are detected by the control module and interpreted by the control module as a change in a level of moisture detected by the moisture detector;
   the moisture detector is situated in a place where if the water heater has a leak, moisture from the leak would gather at the place;
   a first level of voltage indicates a lack of moisture in the place where the moisture detector is situated;
   a second level of voltage indicates wetness in the place where the moisture detector is situated;
   a third level of voltage indicates a condition of moisture between a lack of moisture and wetness in the place where the moisture detector is situated
   when the third level of voltage is between the first level of voltage and the second level of voltage, no action is needed relative to the water heater having a leak; and
   when the third level of voltage is at the second level of voltage, action is needed relative to the water heater having a leak.

8. The method of claim 7, further comprising equating an amount of a change of voltage of the voltage source, detected by the control module to an amount of change of moisture detected by the moisture detector.

9. The method of claim 7, wherein:
   when the third level of voltage is at the first level of voltage detected by the control module, no action is needed relative to the water heater; and
   when the third level of voltage is at the second level of voltage detected by the control module, the control module goes into a pilot light only mode for the water heater, flashes an error code, shuts down the water heater, sounds an audible alarm, or sends an electronic message to indicate that action is needed to prevent or minimize water damage caused by a leak in the water heater.

10. The method of claim 9, wherein:
the control module is powered by the voltage source; and
the voltage source is an item selected from a group comprising thermopiles, line power, batteries, solar cells, charged super capacitors, and wind generators.

11. An appliance leak detection system comprising:
a leak sensor, the leak sensor having a resistance that changes according to an amount of dampness or wetness detected by the leak sensor;
a control module connected to an appliance; and
a voltage source connected to the leak sensor and the control module such that a magnitude of voltage from the voltage source is present at the control module and when a resistance of the leak sensor changes, the magnitude of voltage present at the control module changes; and wherein:
the appliance is selected from a group comprising a water heater, a dishwasher and a washing machine; and
the leak sensor is located in an area where dampness or wetness would appear if the appliance had a leak, and would be sensed by the leak sensor such that an amount of dampness or wetness detected by the leak sensor varies from a dry condition to a wet condition;
the dry condition indicates zero percent moisture and the wet condition indicates one hundred percent moisture; and
a level one is a dry condition;
a level two is a predetermined percent of moisture greater than zero percent;
a level three is a predetermined percentage of moisture greater than that of level two and less than one hundred percent moisture; and
a level four is a wet condition.

12. The system of claim 11, wherein:
the leak sensor has a resistance of an open circuit when situated in an area of dryness and has a resistance of a short circuit when situated in an area of wetness, or the leak sensor has a resistance of a closed circuit when situated in an area of dryness and has a resistance of an open circuit when situated in an area of wetness; and
the leak sensor is selected from a group of items comprising non-discrete variable resistance moisture detectors, discrete variable resistance moisture detectors and moisture sensitive switches.

13. The system of claim 11, wherein when the magnitude of voltage present at the control module changes, the control module recognizes a change of an amount of dampness or wetness detected by the leak sensor.

14. The system of claim 11, wherein:
at level one the control module operates in a routine manner;
at level two, the control module operates in a routine manner;
at level three the control module flashes an error code, changes an operating level or reduces a water temperature set point of the appliance, or sends a Wi-Fi signal to indicate a presence of moisture, or shuts down the appliance and sounds an audible alarm; and
at level four, the control module goes to an idle mode for the appliance, flashes an error code, shuts down the appliance, sounds an audible alarm, or sends a Wi-Fi signal indicating that action is needed to prevent water damage.

15. The system of claim 11, wherein the voltage source is selected from a group comprising thermopiles, line power, batteries, solar cells, charged super capacitors, and wind generators.

* * * * *